United States Patent [19]

Walraevens et al.

[11] Patent Number: 5,318,673
[45] Date of Patent: Jun. 7, 1994

[54] PROCESS FOR THE PURIFICATION OF 1,1-DICHLORO-1-FLUOROETHANE

[75] Inventors: René Walraevens, Brussels; Francine Janssens, Vilvoorde; Jean-Pierre Catinat, Binche, all of Belgium

[73] Assignee: Solvay (Societe Anonyme), Brussels, Belgium

[21] Appl. No.: 43,310

[22] Filed: Apr. 6, 1993

[30] Foreign Application Priority Data

Apr. 17, 1992 [BE] Belgium .............................. 09200357

[51] Int. Cl.$^5$ .............................................. B01D 3/34
[52] U.S. Cl. ....................................... 203/29; 203/38; 203/DIG. 6; 570/178
[58] Field of Search ..................... 203/29, DIG. 6, 91, 203/38; 570/178

[56] References Cited

FOREIGN PATENT DOCUMENTS

| 6235890 | 3/1991 | Australia . | |
|---|---|---|---|
| 0401493A2 | 12/1990 | European Pat. Off. . | |
| 0420709A1 | 4/1991 | European Pat. Off. . | |
| 2-129209 | 5/1990 | Japan | 570/178 |
| 4-264039 | 9/1992 | Japan | 570/178 |
| 1401541 | 7/1975 | United Kingdom . | |

OTHER PUBLICATIONS

CA 115 (5): 48834V "Purification of 1,1-dichloro-1-fluoro ethane," Correia, Yves et al F.

*Primary Examiner*—Virginia Manoharan
*Attorney, Agent, or Firm*—Spencer, Frank & Schneider

[57] ABSTRACT

Process for the purification of crude 1,1-dichloro-1-fluoroethane by treatment with chlorine in the presence of an organic free radical initiator and then distillation.

10 Claims, No Drawings

PROCESS FOR THE PURIFICATION OF 1,1-DICHLORO-1-FLUOROETHANE

BACKGROUND OF THE INVENTION

1. Field of the Invention

The present invention relates to an improved process for the purification of crude 1,1-dichloro-1-fluoroethane by treatment with chlorine followed by distillation.

2. Description of the Related Art 1,1-Dichloro-1-fluoroethane (HFA-141b) is a partially halogenated chlorofluorinated hydrocarbon which is proving to be an advantageous substitute for certain entirely halogenated chlorofluorinated hydrocarbons (CFCs) whose production and use are being progressively reduced because they are suspected of having a harmful effect on the ozone layer.

Crude 1,1-dichloro-1-fluoroethane from the synthesis processes is generally contaminated by by-products of the synthesis and undesirable impurities. Certain of these by-products and impurities can be easily separated by distillation. This is especially the case for 1-chloro-1,1-difluoroethane, 1,1,1-trifluoroethane or 1,1,1-trichloroethane, as well as for the heavier compounds comprising a greater number of carbon atoms, formed during the reaction. However, 1,1-dichloro-1-fluoroethane generally contains as impurities small amounts of chlorinated and/or chlorofluorinated unsaturated compounds whose separation by distillation proves to be difficult, in view of their boiling point in the neighborhood of that of 1,1-dichloro-1-fluoroethane.

Besides vinylidene chloride, which is the most important impurity, the unsaturated impurities which may be present in 1,1-dichloro-1-fluoroethane to be purified are mainly cis- and trans-1,2-dichlorofluoroethylenes, trans-1,2-dichloroethylene, dichloroacetylene and 1-chloro-1-fluoroethylene.

Patent Application EP-A-0,401,493 from Atochem North America describes the purification of 1,1-dichloro-1-fluoroethane by photochemical chlorination of the unsaturated impurities followed by a separation by distillation. This process is implemented at a temperature such that 1,1-dichloro-1-fluoroethane is in the liquid phase at the operating pressure. The operating conditions are also in part limited by the presence of the light energy source.

The accent is put in this document on the purification from vinylidene chloride but, in the majority of the examples, it was not possible to fall below 120 ppm by weight of this compound. Additionally, the removal of cis- and trans-1,2-dichlorofluoroethylenes was not mentioned, which are more halogenated impurities whose conversion appears more difficult as, in certain cases, their concentration can increase again after having passed through a minimum. By way of reference, let it be pointed out that the PAFT II specifications (Program for Alternative Fluorocarbon Toxicity testing) impose a total chlorofluorinated unsaturated impurities content not exceeding 10 ppm by weight.

The present invention consequently has the aim of providing an improved process for the purification of crude 1,1-dichloro-1-fluoroethane by treatment with chlorine followed by a distillation which not only makes possible a better purification from vinylidene chloride but also an effective and rapid separation from the other unsaturated impurities, especially cis- and trans-1,2-dichlorofluoroethylenes.

SUMMARY OF THE INVENTION

For this purpose, the invention relates to a process for the purification of crude 1,1-dichloro-1-fluoroethane by treatment with chlorine and then distillation, the treatment with chlorine being carried out in the presence of an organic free radical initiator.

In the process according to the invention, crude 1,1-dichloro-1-fluoroethane is understood to denote 1,1-dichloro-1-fluoroethane and the impurities (including in this the by-products of its manufacture) which it contains.

In order to promote mixing of the crude 1,1-dichloro-1-fluoroethane with the organic initiator, the process according to the invention is preferably carried out in the liquid phase.

The organic free radical initiator has the function of decomposing the chlorine molecules by free radical splitting. According to the invention, the free radical initiator is an organic compound. Among the organic compounds, the peroxide or diazo compounds are most often used. In particular, the peroxide compounds are used. Among these, more particularly the diacyl peroxides, peroxydicarbonates, alkyl peresters, peracetals, ketone peroxides, alkyl hydroperoxides or dialkyl peroxides are chosen. Preferably, the diacyl peroxides or peroxydicarbonates are retained. Excellent results have been obtained with dilauroyl peroxide, dibenzoyl peroxide or dicetyl peroxydicarbonate. The organic initiator is preferably selected from the compounds having a half-life of 0.1 to 3 hours and, most often, of approximately 1 hour at the temperature of the treatment with chlorine.

The organic initiator may be used at very variable doses. It is generally used at a concentration of at least approximately 10 ppm by weight with respect to the crude 1,1-dichloro-1-fluoroethane. In particular, at least approximately 20 ppm by weight of organic initiator are used and more particularly still at least approximately 30 ppm by weight. Most often, not more than approximately 10,000 ppm by weight are used of organic initiator with respect to the crude 1,1-dichloro-1-fluoroethane. Preferably, a figure of approximately 1000 ppm by weight of organic initiator and more preferentially still a figure of approximately 300 ppm by weight is not exceeded.

The treatment with chlorine has the function of chlorinating the unsaturated impurities of the crude 1,1-dichloro-1-fluoroethane. It especially has the function of converting vinylidene chloride, the cis- and trans -1,2-dichlorofluoroethylenes and dichloroacetylene.

The chlorine can be used in the gaseous phase or in the liquid phase. It is introduced, in excess amounts with respect to all the unsaturated impurities to be chlorinated, into the crude 1,1-dichloro-1-fluoroethane.

Generally, the chlorine is used in a ratio of more than 3 mol per mole of unsaturated impurities, preferably at least approximately 4 mol per mole of unsaturated impurities. Most often, it is not desirable to exceed approximately 40 mol of chlorine per mole of unsaturated impurities. It is preferable to limit the amount used in order that virtually all the chlorine can react and is not found as such downstream from the present purification treatment. Preferably, a ratio of approximately 15 mol per mole of unsaturated impurities is not exceeded and more preferentially still this ratio does not exceed approximately 12.

The treatment with chlorine can be carried out in a wide range of temperatures. In particular, the treatment with chlorine is carried out at a temperature of at least approximately 40° C. and more particularly still of more than approximately 60° C. Higher temperatures make possible a faster conversion of the unsaturated compounds, more particularly of the 1,2-dichlorofluoroethylenes, without it being possible for too much formation of heavy compounds to result from parallel substitutive chlorination reactions. However, a correlative increase in the pressure results therefrom which it is advisable to take into account. Preferably, the treatment temperature does not exceed approximately 150° C. and, more preferentially still, it does not exceed approximately 100° C. Excellent results have been obtained when the treatment with chlorine is carried out at approximately from 60° to 100° C.

The treatment with chlorine can be carried out at autogenous pressure or a greater pressure generated by the introduction of an inert gas. In general, the treatment is carried out at a pressure which does not exceed approximately 5 MPa, preferably 2 MPa. Pressures from approximately 0.2 to approximately 1.0 MPa are highly suitable.

These correlated high pressure and temperature conditions allowed for the treatment with chlorine contribute to the efficient and rapid removal of the unsaturated impurities.

The duration of the treatment with chlorine can be from approximately 1 to approximately 120 minutes. Preferably, the duration of the treatment with chlorine is at most approximately 60 minutes.

In the presence of a significant excess of chlorine, the duration of the treatment will be altered in order to limit losses of 1,1-dichloro-1-fluoroethane by substitutive chlorination and formation of 1,1,2-trichloro-1-fluoroethane.

The presence will also be limited of metal ions which could be the origin of the reformation of cis- and trans-1,2-dichlorofluoroethylenes, by dehydrochlorination of the abovementioned 1,1,2-trichloro-1-fluoroethane. This explanation does not, however, bind the Applicant.

The chlorination reactor and the distillation devices are consequently preferably made with corrosion-resistant materials, such as especially the alloys of Monel, Inconel or Hastelloy type.

During the treatment with chlorine, it is seen to that the oxygen content in the chlorine is less than 1000 ppm by volume and preferably that it does not exceed 50 ppm by volume. To do this, the crude 1,1-dichloro-1-fluoroethane is first deaerated by sparging with an inert gas, for example nitrogen.

The distillation which follows the treatment with chlorine has the function of separating the impurities from 1,1-dichloro-1-fluoroethane, after their chlorination. The distillation can be carried out by any known conventional means.

According to an advantageous variant embodiment of the process according to the invention, the organic initiator is introduced into the crude 1,1-dichloro-1-fluoroethane before the chlorine. In a preferred variant of carrying out this embodiment of the invention, the chlorine is introduced into the 1,1-dichloro-1-fluoro -ethane at a temperature in the region of that of the treatment. In a particularly preferred variant of carrying out this embodiment of the invention, the organic initiator is also introduced into the 1,1-dichloro-1-fluoroethane at a temperature in the region of that of the treatment.

The process according to the invention applies to the purification of crude 1,1-dichloro-1-fluoroethane prepared by any synthesis process, without a prior treatment being required. The process according to the invention finds an advantageous application in the purification of 1,1-dichloro-1-fluoroethane obtained by synthesis from vinylidene chloride and hydrogen fluoride. The process according to the invention can especially be used in the presence of compounds whose boiling point is substantially greater than that of 1,1-dichloro-1-fluoro -ethane. Preferably, these compounds are, however, separated beforehand from the 1,1-dichloro-1-fluoroethane. It is also preferable to separate beforehand the compounds whose boiling point is substantially less than that of 1,1-dichloro-1-fluoro -ethane, such as especially 1-chloro-1,1-difluoroethane and 1,1,1-trifluoroethane. These separations can be carried out conventionally by distillation.

DESCRIPTION OF THE PREFERRED EMBODIMENTS

Examples 1 to 3 illustrate the invention In a non-limiting way. Example 4R is given by way of reference.

EXAMPLES

Example 1

300 ml of crude 1,1-dichloro-1-fluoroethane, containing 110 ppm by weight of dilauroyl peroxide (half-life of 1 h at 80° C.) were introduced, by suction, into a 0.5 l autoclave made of Hastelloy alloy, equipped with a stirrer, cooled beforehand to 0° C. and put under a vacuum of 1,500 Pa. The solution, maintained at 0° C., was then deaerated by repeatedly passing nitrogen through.

The reaction mixture was then brought to 76° C. by immersing the reactor in a preheated thermostatically controlled bath. The pressure, at this stage, was $4.2.10^5$ Pa.

3 g of chlorine, i.e. 5.2 mol of chlorine per mole of unsaturated impurities, were then introduced. The temperature rose to 81° C. and was maintained at this value whereas the autogenous pressure increased to reach $5.2.10^5$ Pa after 23 minutes.

Samples were withdrawn during the test, using a sample tube. They were collected directly in a flask containing 50 ml of a saturated aqueous sodium bicarbonate solution, cooled beforehand in ice. After decanting and drying over $CaCl_2$, the organic phase collected was analyzed by gas phase chromatography.

Table 1 shows the contents of unsaturated impurities in $mg.kg^{-1}$ in the crude 1,1-dichloro-1-fluoroethane, before introduction of chlorine and then 23 minutes after introduction of chlorine.

TABLE 1

| Unsaturated compound | Initial reaction mixture | After treatment t = 23 min |
| --- | --- | --- |
| Vinylidene chloride | 850 | <2 |
| Dichloroacetylene | 228 | <1 |
| trans-1,2-Dichloroethylene | 920 | <1 |
| cis-1,2-Dichlorofluoroethylene | 79 | <1 |
| trans-1,2-Dichlorofluoroethylene | 43 | <2 |

TABLE 1-continued

| Unsaturated compound | Initial reaction mixture | After treatment t = 23 min |
|---|---|---|
| 1-Chloro-1-fluoroethylene | 2 | <1 |

These results illustrate that, after only 23 minutes of treatment, there only remains less than 2 ppm by weight of each of the unsaturated impurities present, especially vinylidene chloride and cis- and trans-1,2-dichlorofluoroethylenes. It is thus possible, by distillation, to obtain 1,1-dichloro-1-fluoroethane of high purity.

Example 2

300 ml of crude 1,1-dichloro-1-fluoroethane, containing 71 ppm by weight of dibenzoyl peroxide (half-life of 1 h at 91° C) were introduced into an autoclave identical to that of Example 1 and in the same way. The solution, maintained at 0° C., was then deaerated by repeatedly passing nitrogen through.

The reaction mixture was then brought to 92° C. by immersing the reactor in a preheated thermostatically controlled bath. The pressure, at this stage, was $6.3 \cdot 10^5$ Pa.

4.8 g of chlorine, i.e. 8 mol of chlorine per mole of unsaturated impurities, were then introduced. The temperature rose to 96° C. and was maintained at this value whereas the autogenous pressure increased to reach $7.10^5$ Pa after 15 minutes.

Samples were withdrawn during the test and analyzed as in Example 1.

Table 2 shows the contents of chlorinated and chlorofluorinated unsaturated impurities in mg.kg$^{-1}$ in the crude 1,1-dichloro-1-fluoroethane, before introduction of chlorine and then 15 minutes after introduction of chlorine.

TABLE 2

| Unsaturated compound | Initial reaction mixture | After treatment t = 15 min |
|---|---|---|
| Vinylidene chloride | 863 | <2 |
| Dichloroacetylene | 230 | <1 |
| trans-1,2-Dichloroethylene | 937 | <1 |
| cis-1,2-Dichlorofluoroethylene | 80 | <1 |
| trans-1,2-Dichlorofluoroethylene | 42 | <1 |
| 1-Chloro-1-fluoroethylene | 2 | <1 |

Example 3

300 ml of crude 1,1-dichloro-1-fluoroethane, containing 156 ppm by weight of dicetyl peroxydicarbonate (half-life of 1 h at 57° C.) were introduced into an autoclave identical to that of Example 1 and in the same way. The solution, maintained at 0° C., was then deaerated by repeatedly passing nitrogen through.

The reaction mixture was then brought to 57° C. by immersing the reactor in a preheated thermostatically controlled bath. The pressure, at this stage, was $2.9 \cdot 10^5$ Pa.

4.8 g of chlorine, i.e. 11 mol of chlorine per mole of unsaturated impurities, were then introduced. The temperature rose to 63° C. and was maintained at this value whereas the autogenous pressure increased to reach $3.8 \cdot 10^5$ Pa after 22 minutes.

Samples were withdrawn during the test and analyzed as in Example 1.

Table 3 shows the contents of chlorinated and chlorofluorinated unsaturated impurities in mg.kg$^{-1}$ in the crude 1,1-dichloro-1-fluoroethane, before introduction of chlorine and then 22 minutes after introduction of chlorine.

TABLE 3

| Unsaturated compound | Initial reaction mixture | After treatment t = 22 min |
|---|---|---|
| Vinylidene chloride | 879 | <1 |
| Dichloroacetylene | 291 | <1 |
| trans-1,2-Dichloroethylene | 945 | 3 |
| cis-1,2-Dichlorofluoroethylene | 84 | 1 |
| trans-1,2-Dichlorofluoroethylene | 47 | <1 |
| 1-Chloro-1-fluoroethylene | 1 | <1 |

Example 4R (for reference)

10 g of crude 1,1-dichloro-1-fluoroethane were introduced at room temperature into a 10 ml flask. An amount of gaseous chlorine corresponding to 3 mol of chlorine per mole of unsaturated impurities was then introduced, in a single step, using a syringe, through the Teflon stopper closing the flask.

The sample was then exposed to the radiation from a Philips HP 80 UV lamp in a closed chamber (lamp/sample distance: 15 cm). The temperature was maintained at approximately 35° C. by circulating air in the chamber.

The sample was then analyzed by gas phase chromatography.

Table 4 shows the contents of chlorinated and chlorofluorinated unsaturated impurities in mg.kg$^{-1}$ in the crude 1,1-dichloro-1-fluoroethane, before introduction of chlorine and then 2.5 h and 8 h after introduction of chlorine.

TABLE 4

| Unsaturated compound | Initial reaction mixture | After treatment t = 2.5 h | After treatment t = 8h |
|---|---|---|---|
| Vinylidene chloride | 295 | 3 | <1 |
| Dichloroacetylene | 6 | <1 | <1 |
| trans-1,2-Dichloroethylene | 189 | 5 | 13 |
| cis-1,2-Dichlorofluoroethylene | 110 | 5 | 7 |
| trans-1,2-Dichlorofluoroethylene | 114 | 9 | 10 |
| 1-Chloro-1-fluoroethylene | 12 | 2 | 3 |

This reference example illustrates that the complete chlorination of vinylidene chloride photochemically demands a very long treatment time and that, even in this case, cis- and trans-1,2-dichloro -fluoroethylenes and 1-chloro-1-fluoroethylene remain present in amounts which are significant with respect to the results obtained with the process according to the present invention.

What is claimed is:

1. A process for the purification of crude 1,1-dichloro-1-fluoroethane containing unsaturated impurities, comprising:
   removing said unsaturated impurities including vinylidene chloride and cis- and trans -1,2-dichlorofluoroethylenes by
   treating the crude 1,1-dichloro-1-fluoroethane with chlorine in the presence of an organic free radical initiator to chlorinate the unsaturated impurities contained therein; and then
   distilling to recover purified 1,1-dichloro-1-fluoroethane.

2. The process according to claim 1, wherein the organic free radical initiator is selected from the group consisting of peroxide or diazo compounds.

3. The process according to claim 2, wherein the organic free radical initiator is at least one peroxide compound.

4. The process according to claim 3, wherein the at least one peroxide compound is selected from the group consisting of diacyl peroxides and peroxydicarbonates.

5. The process according to claim 3, wherein the at least one peroxide compound is selected from the group consisting of dilauroyl peroxide, dibenzoyl peroxide and dicetyl peroxydicarbonate.

6. The process according to claim 1, wherein treatment with chlorine takes place at a treatment temperature and wherein the organic free radical initiator has a half-life of approximately 1 hour at the treatment temperature of the treatment with chlorine.

7. The process according to claim 1, wherein treatment with chlorine is carried out in the presence of at least approximately 10 ppm by weight of the organic free radical initiator with respect to the weight of the crude 1,1-dichloro-1-fluoroethane.

8. The process according to claim 1, wherein the chlorine is used in a ratio of mol of chlorine per mole of unsaturated impurities in the crude 1,1-dichloro-1-fluoroethane which is more than 3 but does not exceed approximately 15.

9. The process according to claim 1, wherein treatment with chlorine is carried out at a treatment temperature ranging from approximately 40 to approximately 150° C.

10. The process according to claim 1, wherein treatment with chlorine has a duration which is at most approximately 60 minutes.

* * * * *